United States Patent [19]

Yamanashi et al.

[11] Patent Number: 5,019,076

[45] Date of Patent: May 28, 1991

[54] RADIO FREQUENCY SURGICAL TOOL AND METHOD

[76] Inventors: William S. Yamanashi, 107 E. G St., Jenks, Okla. 74137; Arun-Angelo Patil, 3709 E. 69th Pl., Tulsa, Okla. 74136

[21] Appl. No.: 449,110

[22] Filed: Dec. 7, 1989

Related U.S. Application Data

[63] Continuation of Ser. No. 906,791, Sep. 12, 1986, abandoned.

[51] Int. Cl.$^5$ .............................. A61B 17/39
[52] U.S. Cl. ......................... 606/45; 606/49
[58] Field of Search ............ 606/33, 41, 45, 49; 128/804, 422, 1.5

[56] References Cited

U.S. PATENT DOCUMENTS

| | | | |
|---|---|---|---|
| 1,807,105 | 5/1931 | Schliephake | 128/804 |
| 3,566,877 | 3/1971 | Smith et al. | 128/804 |
| 4,154,246 | 5/1979 | LeVeen | 128/804 |
| 4,534,347 | 8/1985 | Taylor | 128/303.17 |
| 4,674,481 | 6/1987 | Boddie, Jr. | 128/1.3 |
| 4,682,596 | 7/1987 | Bales et al. | 606/45 X |
| 4,790,311 | 12/1988 | Ruiz | 128/303.1 |

OTHER PUBLICATIONS

Thackray et al., "Indirect Heating Source...", Electrocomponent Science & Tech., vol. 1, No. 2, pp. 91–96, Dec. 1974.

W. S. Yamanashi et al., Field Focusing and Focal Heating Patterns Using Hybrid Radio Frequency Hyperthermia System, *Medical Instrumentation*, vol. 17, No. 5, Sep.–Oct. 1983, pp. 358–364.

Yamanashi et al., Further Observations on Tissue Heating Patterns Using an Invasive Ground Probe with Radio Frequency Hyperthermia System, *Medical Instrumentation*, vol. 18, No. 4, Jul.–Aug. 1984, pp. 220–223.

Yamanashi et al., Focused Hyperthermia, with a Magnetic Resonance Imaging (MRI) Unit and an Interstitial Grounded Probe, *Physiological Chemistry and Physics and Medical NMR*, 16(1984), pp. 491–498.

*Primary Examiner*—Lee S. Cohen
*Attorney, Agent, or Firm*—Head & Johnson

[57] ABSTRACT

A surgical tool and method of surgical treatment involving a radio frequency source (e.g., 13.0 to 28.0 MHz) creating an electromagnetic field in the vicinity of tissue to be surgically treated and a grounded, tuned, electromagnetic field focusing probe that focuses the electromagnetic field energy at the tip of the probe, thus instantaneously vaporizing, cutting and cauterizing the tissue in contact with the probe tip. Such a surgical tool is capable of creating a virtually bloodless, micro-thin incision as well as selectively coagulating body fluids (e.g., blood) and as such, is particularly useful in neuro, oncological and vascular surgery.

24 Claims, 7 Drawing Sheets

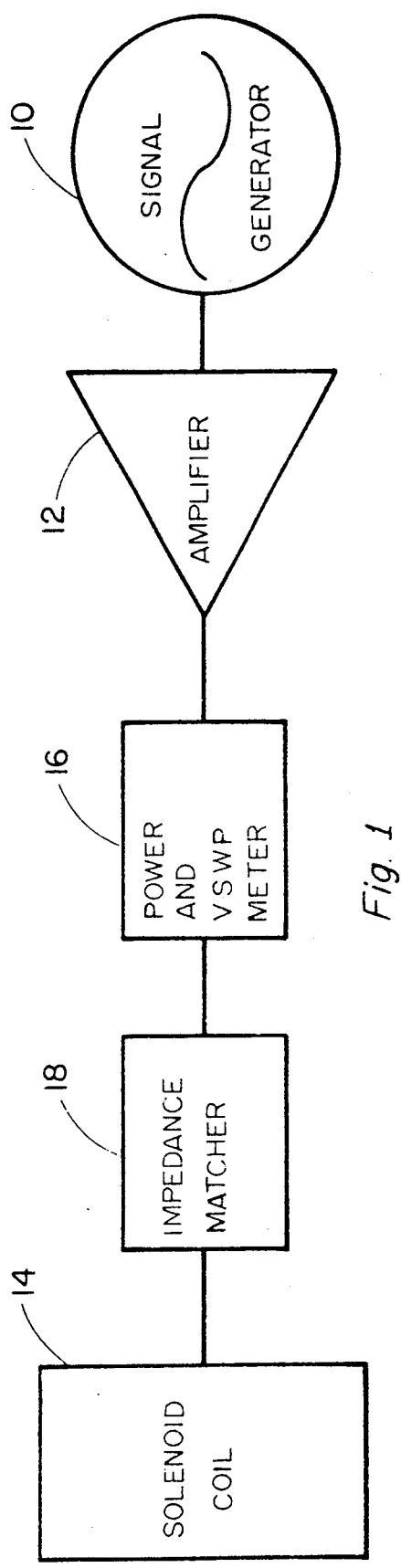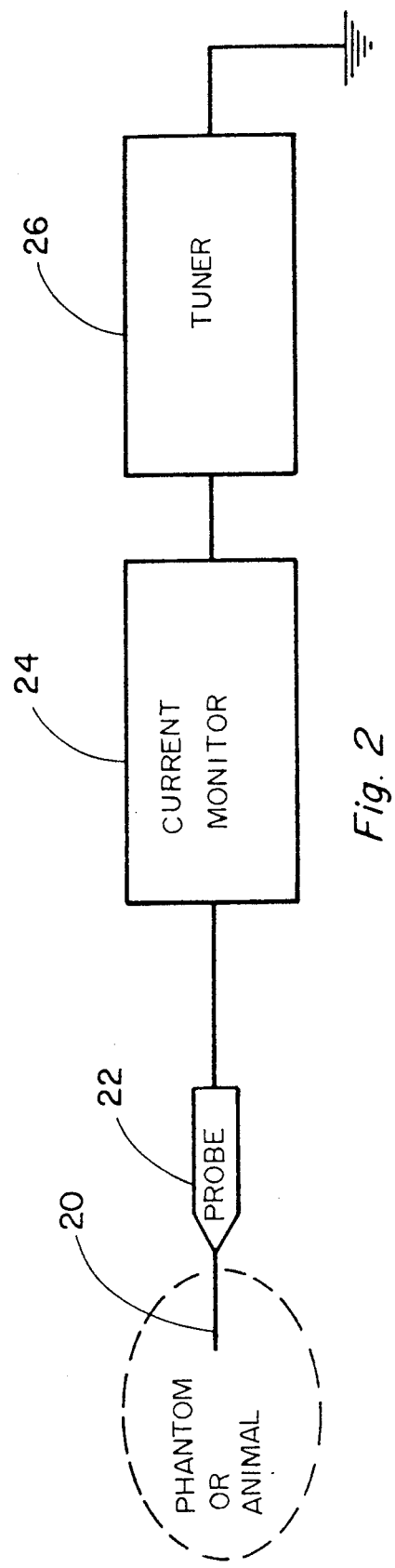

RADIO FREQUENCY SURGICAL TOOL AND METHOD

This is a continuation of copending application Ser. No. 06/906,791, filed on Sept. 12, 1986, now abandoned.

This application is an improvement over co-pending application Ser. No. 546,917 now U.S. Pat. No. 4,674,481, dated Jun. 23, 1987, which is related by reason of common inventor, William S. Yamanashi.

BACKGROUND OF THE INVENTION

1. Field of the Invention

This invention relates to an electromagnetic field focusing (EFF) probe and its use as a surgical scalpel and/or tissue vaporizing and cauterizing instrument. More specifically, the invention relates to a radio frequency surgical knife.

2. Description of the Prior Art

In recent years, the need for certain specific improvements in surgical techniques and tools have led to alternative methods and devices, each possessing certain attributes that are advantageous. For example, the development of laser technology has resulted in new and improved surgical methods and apparatus that can perform incisions with microscopic precision. However, laser surgery does not necessarily result in autocauterization of the incision nor is it necessarily amenable to excising tissue bloodlessly. In contrast, the contemporary electrocauterizer can achieve the excising of tissue bloodlessly, but is not amenable to microscopic precision.

It has also been recently discovered that a commercial magnetic resonance imaging (MRI) scanner can be employed with a grounded interstitial probe to produce relatively localized, small temperature increases in tissue for hperthermic therapeutic treatment. However, prior to the present invention and to the best knowledge of the present Inventors, no one has discovered how to employ electromagnetic field focusing such as to produce a surgical tool that achieves, simultaneously, microscopic precision and bloodless incision.

SUMMARY OF THE INVENTION

In view of the prior art, the present invention provides a new and novel surgical tool and method of use that instantaneously vaporizes tissue along a micro-thin incision line. The method and tool further cauterizes the tissue along the line of incision leading to essentially bloodless surgery. According to the present invention, the energy associated with high-frequency radio waves is focused at the "miniature" probe tip of the electrically tuned surgical tool, thus producing instantaneously, ultra-high temperatures at very localized regions. This in turn results in virtually instantaneous vaporization of the tissue in contact with the microscopic probe. This, the use of the novel tool and surgical method according to the present invention involves surgical treatment of tissue which broadly encompasses cutting, cauterizing and vaporizing along a micro-thin incision as well as coagulation of in situ fluids and as such, the use of the phrase "surgical treatment" when employed in conjunction with the present invention should be appropriately defined to encompass all such features.

Thus, the present invention provides a surgical tool comprising:

(a) a radio frequency source means for creating an electromagnetic field in the vicinity of tissue to be surgically treated; and (b) an electromagnetic field focusing probe means for focusing the radio frequency energy produced by the radio frequency source means at the region of the tissue making contact with the tip of the electromagnetic field focusing probe such that the tissue being contacted is instantaneously vaporized, producing simultaneously a cutting and cauterizing effect.

In one specific embodiment of the surgical tool, the radio frequency source means further comprises:

(a) a signal generator means for producing an oscillating electrical signal of a pre-selected frequency;

(b) an amplifier means connected to said signal generating means for amplifying the oscillating electrical signal;

(c) a meter means for monitoring the amplified oscillating electrical signal output of the signal generating means and the amplifier means;

(d) an impedance matching means for adjusting the impedance between the signal generator means with amplifier means and an inductive applicator means; and (e) an inductive applicator means for inducing the electromagnetic field in the vicinity of the tissue to be surgically treated.

In still another specific embodiment of the surgical tool, the electromagnetic field focusing probe means further comprises:

(a) a conductive metal probe covered with an insulating sheath wherein the tip of the conductive metal probe is exposed at one end such as to allow the tip to make contact with the tissue to be surgically treated and wherein the other end of the conductive metal probe is electrically grounded;

(b) a current monitor means for measuring the electrical current induced in the conductive metal probe during use of the surgical tool; and (c) a tuner circuit means for adjusting and optimizing the induced electrical current passing through the conductive metal probe.

For manual operation, the conductive metal probe can preferably be a hand-held scalpel with the cutting edge being an exposed metal tip of an otherwise grounded insulated wire extending out of the handle. While for applications involving an endocscope of the like, the conductive metal probe is an insulated wire catheter like instrument with an exposed wire tip. Optionally, the probe can be further equipped with a vacuum tube terminating in the vicinity of the surgical tip, such as to remove vaporized tissue and fluids.

The process or method of surgical treatment according to the present invention involves the steps of:

(a) creating an electromagnetic field in the vicinity of tissue to be surgically treated; and (b) touching the tissue to be surgically treated with the exposed metal tip of a grounded electromagnetic field focusing probe such as to instantaneously vaporize the tissue being contacted by the metal tip and producing simultaneously a cutting and cauterizing effect.

It is an object of the present invention to provide both a surgical tool and method of surgical treatment that creates a micro-thin incision by simultaneously cutting and cauterizing tissue. It is a further object that the cutting and cauterizing be achieved simultaneously without bleeding. It is still a further object that the tool and method employ a radio frequency field and an electromagnetic field focusing probe to achieve ultra-high high temperatures in a very localized region virtually instantaneously. It is still another object to provide a tool and method of selectively coagulating body fluids. Fulfillment of these objects and the presence and fulfillment of additional objects will become apparent upon complete reading of the specification and claims taken in conjunction with the attached drawings.

BRIEF DESCRIPTION OF THE DRAWINGS

FIG. 1 schematically illustrates the basic components of the radio frequency source according to the present invention.

FIG. 2 schematically illustrates the basic elements of the electromagnetic field focusing (EFF) probe according to the present invention.

DESCRIPTION OF THE PREFERRED EMBODIMENTS

Figure 3:
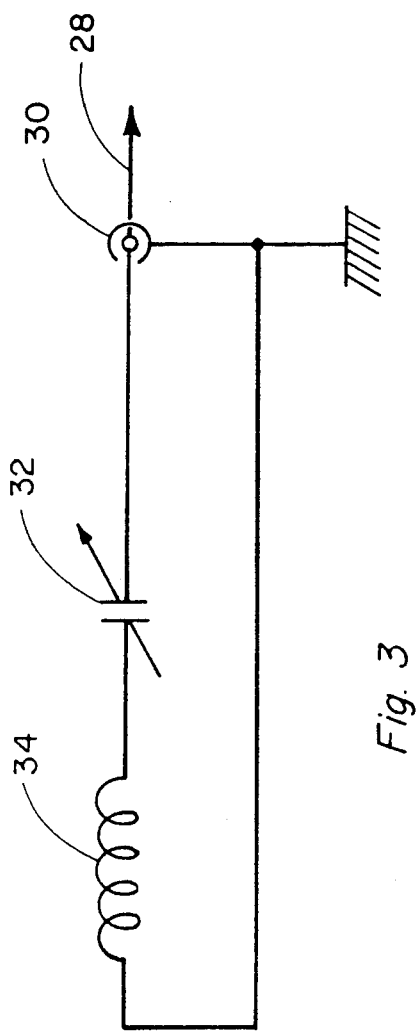
FIG. 3 is a simplified circuit diagram of the inductive applicator portion of the radio frequency source according to the present invention.

The electromagnetic surgical tool system, including the radio frequency source with inductive applicator and the accompanying electromagnetic field focusing (EFF) probe according to the present invention, how they are used and how they function, as well as how they differ from the prior art, can perhaps be best explained and understood by reference to the drawings. FIG. 1 illustrates in a simple block format the individual elements that make up a typical radio frequency source according to the present invention. Generally, the radio frequency source will involve a frequency generator 10 that produces a pre-selected frequency, preferably compatible with operating room conditions. As such, broadly any frequency capable of transmission as an electromagnetic field that can then be focused in a dielectric material such as living tissue by the presence of a tuned, grounded EFF probe is operative for purposes of this invention. Preferably, a high frequency source in the range of 13.0 to 28.0 MHz is to be employed. Consequently, a conventional CB radio may be employed as the frequency source; however, for purposes of this invention, other frequencies and radio bands and associated frequency generators are contemplated as being equivalent to the preferred frequency range.

As further illustrated in FIG. 1, the signal from the frequency generator 10 is amplified by amplifier 12 before being directed to a solenoid coil 14 through a power and VSWR meter 16 and impedance matcher 18. The solenoid coil 14 acts as an inductive applicator in that it induces an electromagnetic field which produces radio frequency (RF) eddy currents in the biological tissue. For purposes of this invention, the inductive applicator can be broadly any transmission antenna configuration that produces an oscillating RF field in the tissue to be surgically treated. As such, various physical configurations and geometries can be employed in the inductive applicator. Preferably, a solenoid coil of wire generally in the shape of an elongated cylinder is to be employed, but other configurations as generally known in the art should be considered equivalent for purposes of this invention. The preferred distance between the solenoid coil and tissue during surgical treatment is from 4 to 7 inches. This preferred range is viewed as a compromise between optimizing the induced electromagnetic field and allowing the surgeon sufficient space to operate. As such, any other convenient distance should be considered equivalent for purposes of this invention.

FIG. 2 illustrates in a block format the basic elements making up a typical electromagnetic field focusing probe according to the present invention. As illustrated, the exposed metal tip 20 (as explained in more detail later) of the probe 22 is intended to make contact with the animal tissue or phantom dielectric material (illustrated in the drawing as dashed lines). In doing so, the energy associated with the RF field induced in the tissue by the radio frequency source illustrated in FIG. 1, is inherently focused or converges at the exposed tip of the probe, thus creating ultra-high temperatures virtually instantaneously. The other end of the probe 22 is grounded through a current monitor 24 and tuner 26.

To further illustrate the basic operation of the radio frequency source or RF field generator of FIG. 1, FIG. 3 shows a partial schematic of the fundamental circuit associated with the solenoid coil or inductive applicator 14. As illustrated, the inductive applicator is connected back to (via line 28) the impedance matcher 18 at a conventional radio frequency connector 30. The amplified RF signal arriving at connector 30 passes through a variable capacitor 32 and RF transmission solenoid coil 34 before being directed to ground.

Figure 5:
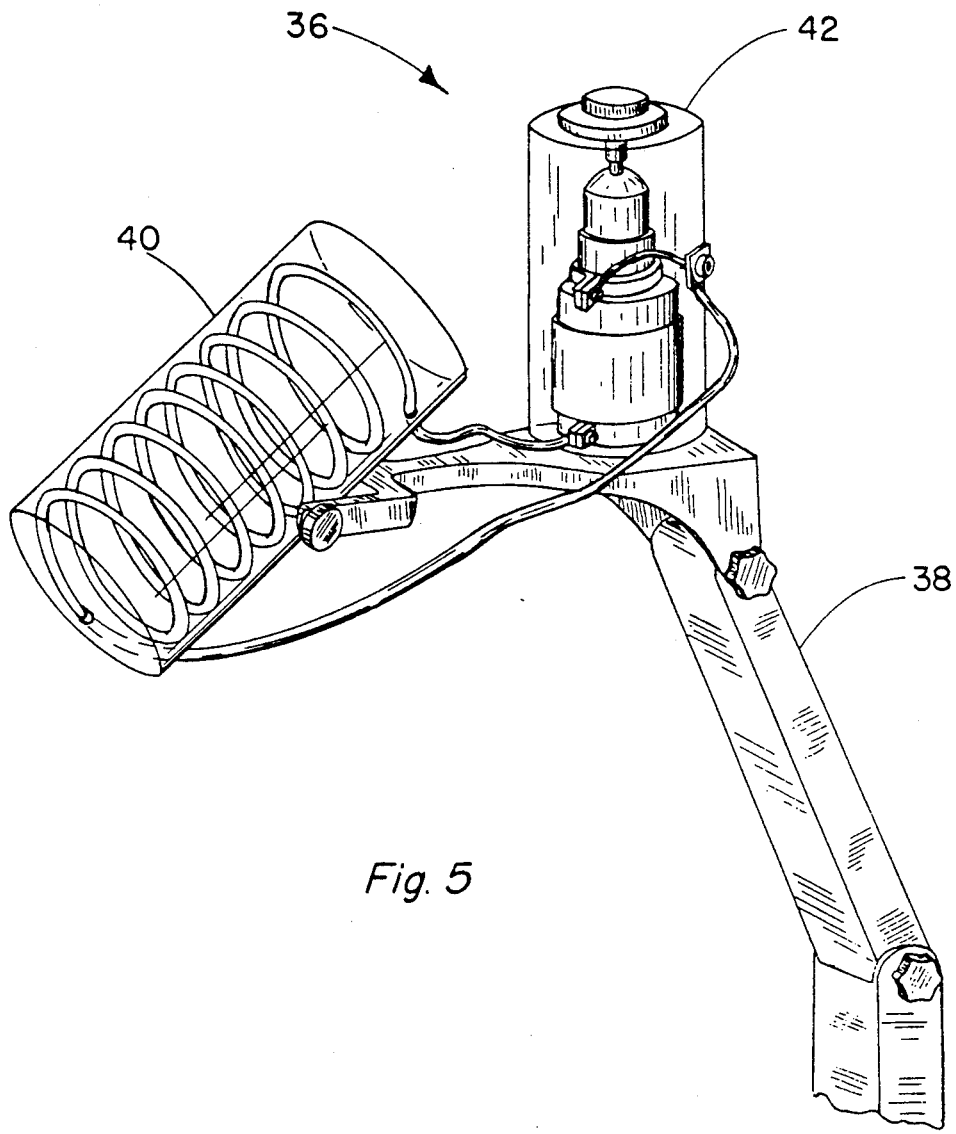
FIG. 5 is a perspective view of an inductive applicator according to the present invention.

FIG. 5 illustrates an actual inductive applicator corresponding to the circuitry of FIG. 3, generally designated by the numeral 36, mounted to an adjustable support member 38 suitable for use in an operating room. As illustrated in FIG. 5, the transmission coil 40 and variable capacitor 42 can be physically moved or positioned over the patient in the vicinity of the tissue to be surgically treated. As such, the coil 40 and the resulting induced electromagnetic field are directed specifically to the region of surgical treatment.

Figure 4:
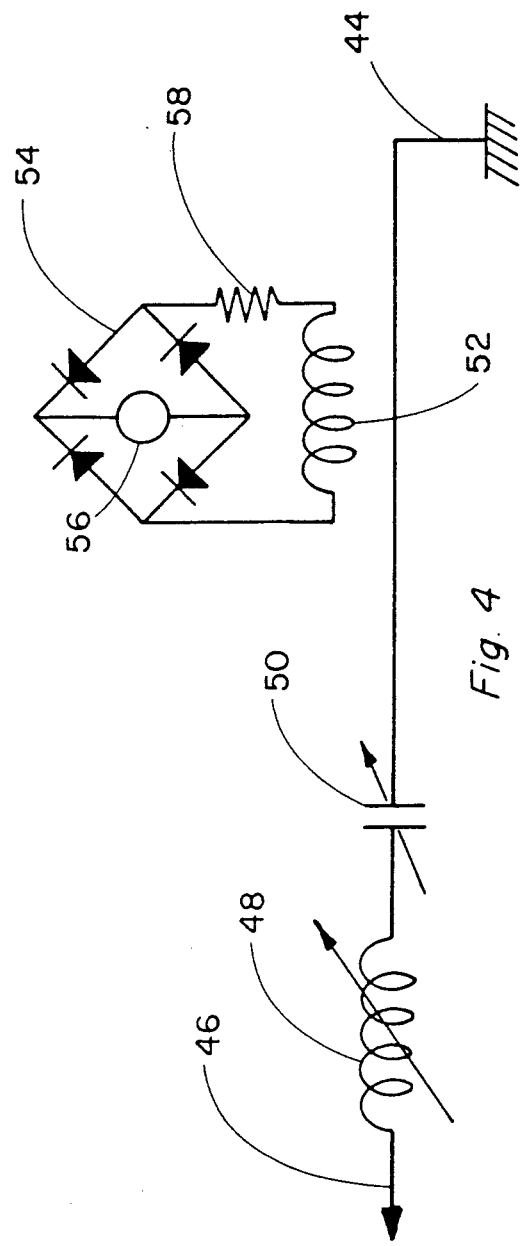
FIG. 4 is a circuit diagram of the grounded EFF probe according to the present invention.

FIG. 4 illustrates a typical schematic of the tuned, grounded, EFF probe according to the present invention. As illustrated, the circuitry is grounded at one end 44 and connected via line 46 to the surgical probe (not shown) at the other end. The tuning of the surgical probe is accomplished by adjusting the variable inductor 48 and variable capacitor 50 located in series with the grounded probe. In order to monitor the effect of the adjustable inductance and capacitance, the current passing to ground is inductively monitored at coil 52 using the diode bridge 54 with meter 56 and feedback resistor 58. In this manner, the probe can be tuned to the particular surgical conditions and frequency source by placing the probe tip in the vicinity of the inductive applicator while the RF source is turned on. The inductance and capacitance of elements 48 and 50 can then be manually adjusted until maximum current is observed at meter 56. A phantom dielectric material can be advantageously employed at this stage prior to actual surgery, thus simulating maximum electromagnetic field convergence (focusing) and optimum temperature rise associated with maximum induced current flow in the surgical probe. Having once tuned the probe in this manner for the particular equipment and RF signal being employed, very little readjustment is found to be necessary.

Figure 6:
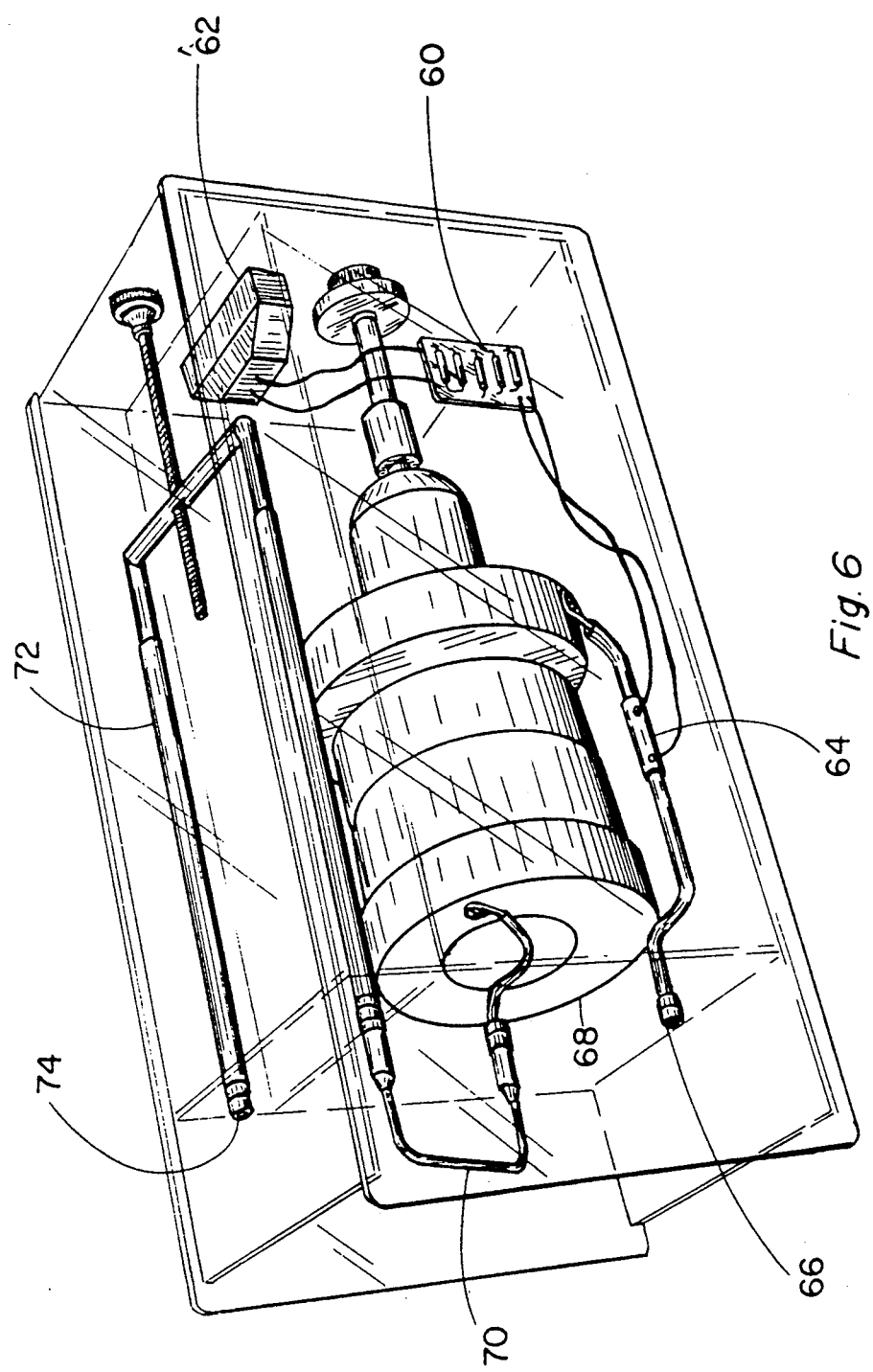
FIG. 6 is a perspective view illustrating the tuner associated with the EFF probe according to the present invention.

FIG. 6 illustrates an actual tuned, grounded, EFF probe circuit corresponding to FIG. 4 and suitable for use in an operating room. As shown, the resistive, diode bridge 60 with meter 62 are connected to an inductive pick-up 64 surrounding lead wire 66 going to ground (not shown) and coming from the variable capacitor 68. The input lead 70 of the variable capacitor 68 is connected to one lead of the variable inductor 72 with the other lead 74 of the variable inductor 72 being connectable to the surgical probe (not shown). As further illustrated in FIGS. 5 and 6, the operating room compatible circuitry components are preferably encased or enclosed, for example, transparent plastic (polymethyl methacrylate, and the like), for protective as well as sanitary reasons. It is also envisioned that under certain conditions, the equipment could be placed in a Farada cage to reduce the possibility of any extraneous RF signals; however, such precautions are considered optional.

Figure 7:
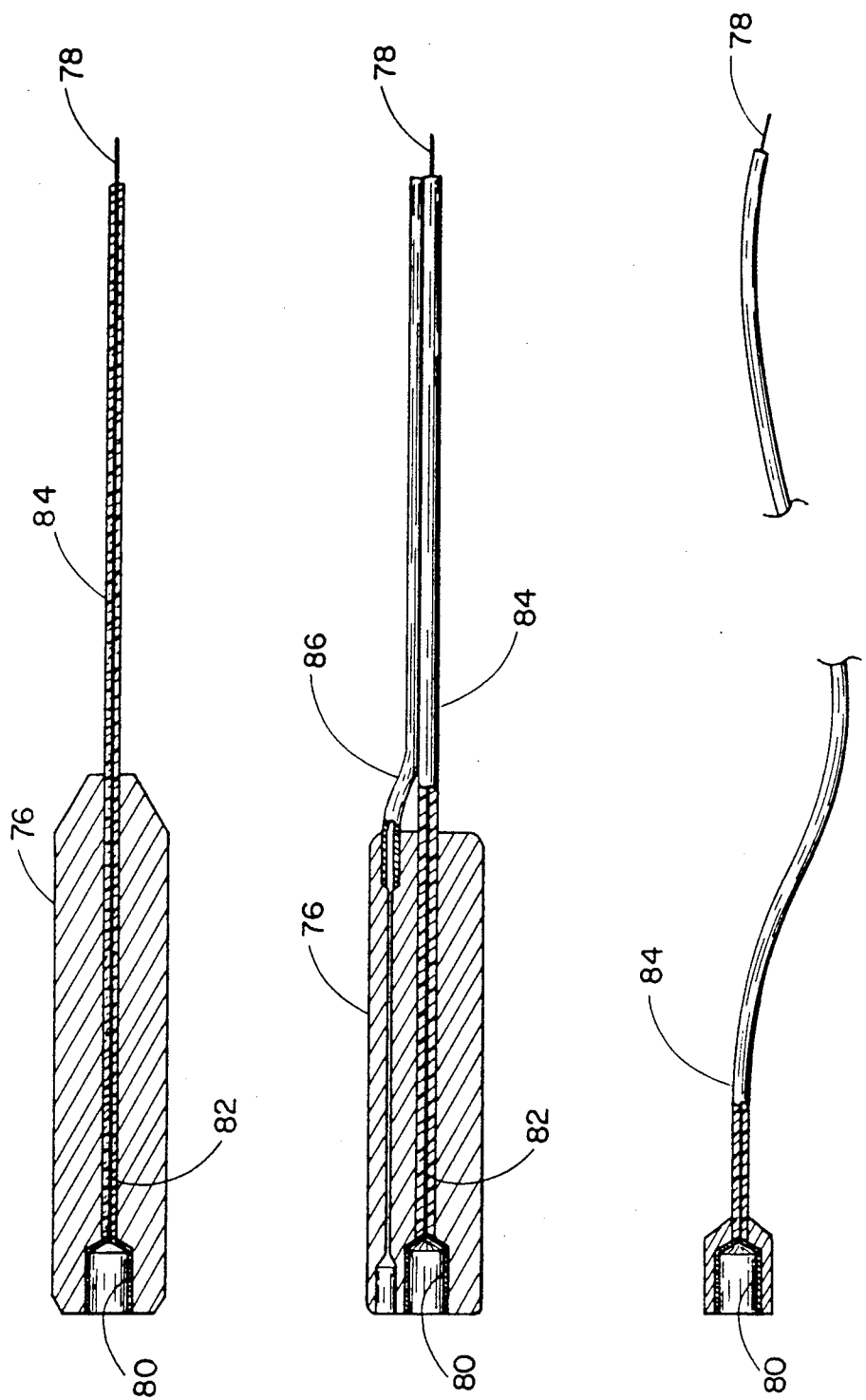
FIG. 7 illustrates a series of surgical probes according to the present invention.

FIG. 7 illustrates a series of typical surgical probes useful in the present invention. As illustrated, each surgical probe consists of a series of essentially equivalent elements and as such, the same number has been used wherever possible to describe the respective embodiments. Typically, the probe comprises a handle member 76, or the equivalent, that is manually held or manipulated by the surgeon during placement and/or surgical movement of the hot tip 78. Recessed in one end of the handle is an electrical connector 80 which is intended to be plugged into a single conductor cable (not shown) that connects to the terminal 74 (see FIG. 6) of the EFF probe circuitry. Passing through the center of the handle is a metal wire 82 that exits the other end of the handle as a shielded (insulated) wire 84. The far end or tip 78 of the insulated wire 84 is exposed (non-insulated) and represents that portion of the probe that converges and focuses the induced electrical field, thus producing high temperatures when touched to the tissue being surgically cut, vaporaized and/or cauterized.

The top probe illustrated in FIG. 7 represents a manually held surgical scalpel probe embodiment of the present invention. Such a probe when used according to the present invention is capable of producing a microthin, bloodless incision and/or instantaneous pyrolysis and vaporization of tumorous tissue and the like. The power output of the probe can vary according to the field strength generated by the RF source and the geometry of the tip of the probe. For example, it has been found that the power output of about 100 to 200 watts can be readily achieved when exposing about 0.7 centimeters of metal tip and at such power level, the surgical tool is particularly useful for neuro surgery and vascular surgery of small blood vessels. Similarly, at higher power levels such as 200 watts to about 600 watts, corresponding typically up to 2.0 centimeters of metal tip exposed, the surgical tool is useful for general surgical procedures including, by way of example, but not limited thereto; laparotomy, lobectomy of liver, resection of gastrointestinal lesions, peritoneum, spleen and kidney.

The center surgical probe illustrated in FIG. 7 is similar to the top embodiment except it is further equipped with a vacuum tube 86 that attaches to a vacuum source (not shown) and terminates near the hot tip of the tool. This particular embodiment is useful in removing vaporized tissue and vaporized fluids generated at the surgical tip of the probe during use.

The lower embodiment shown in FIG. 7 is again similar to the upper embodiment except the shield or insulated wire is considerably longer and no handle, per se, is present. As such, this probe is a catheter like instrument and is intended to be used interstitially including intravenously and the like, including use in combination with an endoscope.

Figure 8:
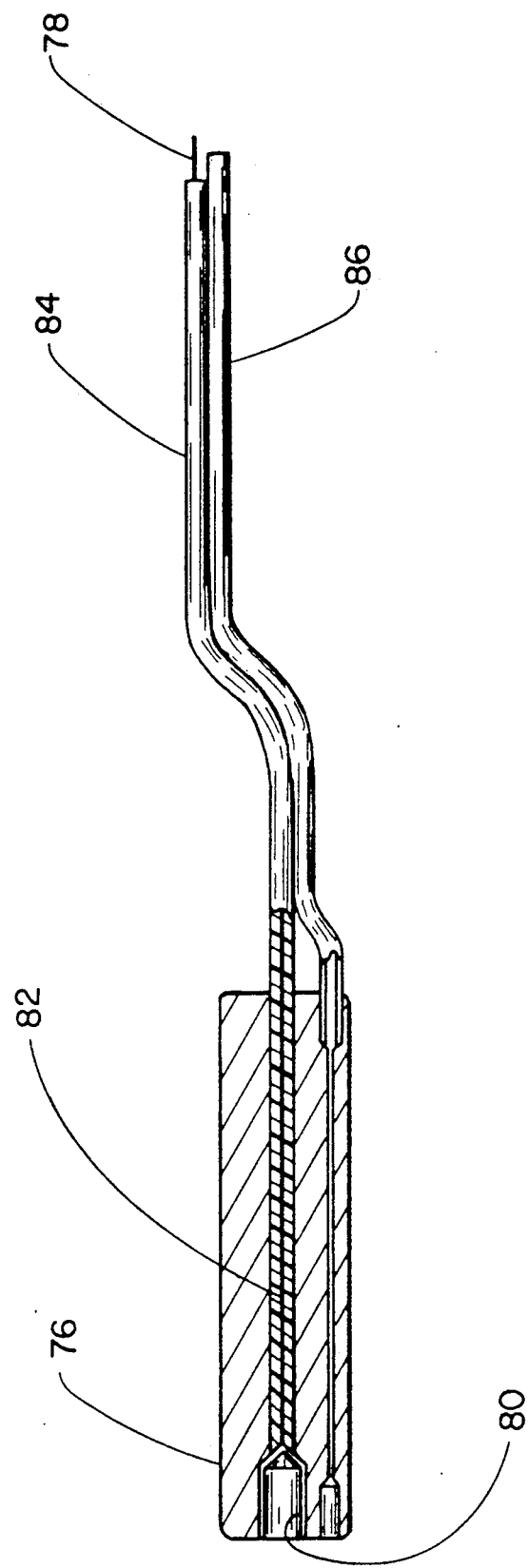
FIG. 8 illustrates another specific embodiment of a surgical probe according to the present invention.

FIG. 8 illustrates another specific embodiment of an EFF probe according to the present invention wherein the insulated wire 84 with exposed tip 78 are accompanied with a vacuum tube 86. In this particularly preferred embodiment, the vacuum tube 86 is below the insulated wire 84 and each are intentionally bent such as to have the tip displaced upwardly from the handle 76 allowing the surgeon improved vision and control of the surgical tip 78.

In describing the above, particularly preferred embodiment of the surgical probe, it should be appreciated that different probe dimensions and types are contemplated for use in the present invention and as such, are considered equivalent for purposes of this invention. The other envisioned embodiments would include by way of example, but not limited thereto, such concepts as provision for adjusting the length of the exposed wire, provisions for adjusting the length of the sheathed wire and various types of handles and attachments including methods of attaching the probe to other medical and surgical tools such as to an endoscope or the like.

Figure 9:
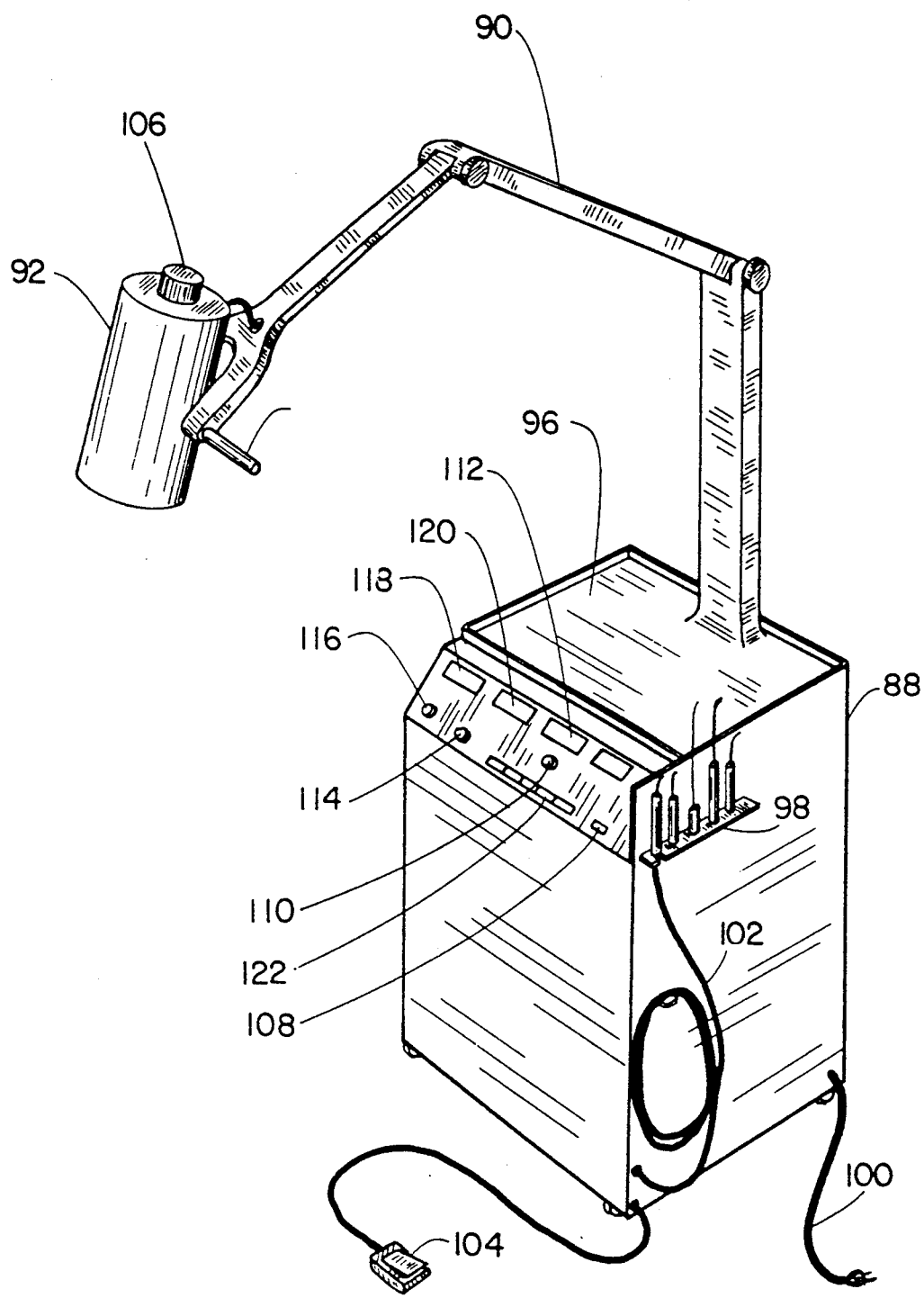
FIG. 9 is a perspective view of an operating room compatible radio frequency surgical tool according to the present invention.

FIG. 9 illustrates another particularly preferred embodiment of the overall RF surgical tool compatible with and suitable for use in an operating room. As illustrated, the surgical unit comprises a cabinet 88 mounted on casters for ease of positioning the flexible arm 90 with inductive applicator 92 (solenoidal coil with variable capacitor) directly over a patient during surgery. To assist in positioning the coil within the applicator near the tissue to be surgically treated, a manual handle 94 is provided to rotate the solenoidal coil and raise/lower or extend/retract the solenoidal coil along the flexible arm. The top of the cabinet 88 is conveniently used as a tray 96 with the plurality of interchangeable EFF probes 98 mounted to one side of the cabinet 88. A conventional 120 volt (30 amps) grounded plug is used as the sole source of power for the RF generator, vacuum source and ancillary equipment mounted within the cabinet 88.

During use of the equipment, the selected probe 98 is attached to grounded cable (with vacuum tube) 102 and held by the surgeon with the inductive applicator 92 positioned over the patient. The surgeon then uses foot pedal 104 to turn the RF field generator on and off as desired. The variable capacitor setting for adjustment for the inductive applicator is provided as a knob 106 near the manually positioned solenoidal coil. The rest of the electronic adjustments and meters are provided on the instrument panel of the cabinet and include typically, a power on/off switch 108; a probe tuner know 110 with probe current meter 112, an analog load 114 and analog tuner 116 adjustment knobs with RF power meter 118 and VSWR power meter 120; along with a set of preset power level switches 122 for different probe types.

The actual construction of the radio frequency surgical tool according to the present invention can be from any of the conventional materials as generally known and employed in the medical and surgical art, provided that the presence of the RF field is taken into consideration. As such, all conductive metal wires and the like (except for the exposed metal tip of the probe) are to be insulated. Various polymers can be used for such purposes, including by way of example, but not limited thereto; polyolefin such as polyethylene and polypropylene, polystyrene, polyfluorohydrocarbons, polyvinyl chlorides and the like. Preferably, the structural components such as the adjustable support arm for holding the inductive applicator and the enclosures for isolating the inductive applicator and probe circuitry are to be made out of structural plastic or similar materials that are essentially transparent (non-absorptive) in the RF range being employed. Such structural plastics would include by way of example, but not limited thereto; polycarbonates, polyamides and/or polyamide/imides, polymethyl methacrylates and other polyacrylates or acrylic polymers, polyolefins and fiber reinforced thermoplastics. The surgical probe cable or wire and probe handle should also be well insulated in the RF sense such that the capacitive coupling to the surgeon's hand or arm is minimum. As such, the ability to withstand up to 20 amps is preferred. The total length of the probe plus probe cable and inductive tuner should be a fractional multiple of the wavelength being employed (e.g., one-half, one-fourth, or five-eights lambda, preferably five-eights wavelength is to be employed).

In order to demonstrate the efficacy of the RF surgical tool and method of surgery according to the present invention, a prototype unit, essentially as illustrated in the drawings, FIGS. 5 and 6, and various EFF probes were assembled and tested. The radio frequency source was assembled essentially as shown in FIGS. 1 and 3, except the amplifier used was a pair of linear amplifiers in series. The following list of equipment was used to assemble the prototype unit:

| Item | Commercial Source or Description |
| --- | --- |
| Signal generator | Hewlett-Packard Model 3314 Function generator (operated at 13.56 MHz and 0.461 volts) |
| Amplifier | ENI Model 350 L, RF amplifier, 50 dB Gain (operated at 35 watts and 0.461 volt input) |
| Amplifier | ETO Model Alpha 76A, RF amplifier, 2 kW max. (operated at 100 to 600 watts and output power level adjusted with "load" and "tune") |
| Power and VSWR meter | Kenwood Model SW-2000 (operated at both 200 watts f.s. and 2 kW f.s.) |
| Impedance matcher | NYE Viking Model M.B. -V-A, Impedance Matching Network, 3000 watt max. (operated with modification to lead push button switch for A.B. and D. channel) |
| Inductive Applicator | Custom constructed solenoidal, air corp 8.3 centimeter diameter, 18.6cm length, 6 § turns, 0.6cm copper tubing, coupled in series with a variable capacitor; ITT-Jennings 50 to 500 pF, 15 kV vacuum bellow variable |

| Item | Commercial Source or Description |
| --- | --- |
| | capacitor |
| Probe tuner | Custom built with a variable inductor; U-shaped configuration and a variable vacuum bellow capactior, ITT-Jennings 50 500 pF |
| Probe current monitor | 20 turns of insulated hook up wire wrapped around a cable connected with the probe tuner and the instrument ground, with a rectifier (full wave), current limited resistor and a 50 nA f.s. DC amp meter |

EXAMPLE I

In order to demonstrate the efficacy of the surgical tool and the method of surgery according to the present invention, a series of laboratory animals were surgically treated using the prototype equipment previously described. In each case, the cutting and vaporizing of the living tissue was accomplished with essentially no visible indication of bleeding during or post surgical treatment. The surgical tip of the probe appeared, in each case, to instantaneously develop very high temperatures leading to essentially instantaneous cutting along a micro-thin incision as the wire tip of the probe made contact with tissue. During the demonstration, the tail of a rat (approximately one inch from the body) and the left ear of a rabbit (approximately one inch from the tip) were completely severed (amputated) with no visible bleeding. A brain lesion created on a rat by conventional surgical techniques was instantaneously cauterized upon contact with the hot tip of the probe, while a liver biopsy was performed on a rat without bleeding. Similarly, a transplanted mammary adenocarcinoma previously introduced subcutaneously on the back of a laboratory mouse was vaporized by repeated contact with the tip of EFF probe, again, in the absence of visible bleeding.

EXAMPLE II

To further evaluate the electromagnetic field focus probe and the overall concept of employing convergence of RF resonance induced Eddy current in biological tissue as an energy source of micro-pryolytic surgery, aneurysms were created and subsequently surgically treated in a series of test animals. The apparatus employed in the treatment of the aneurysms was essentially equivalent to the prototype unit previously described and employed in Example I, except a single linear amplifier was employed to amplify the signal produced by a sign wave oscillator capable of generating 3-30 MHz wide band. The inductive applicator received the amplified signal via a power/SWR meter and an impedance matcher. A solenoid coil was employed to induce the resultant RF electromagnetic field with Eddy current in the biological tissue to be surgically treated. A ⅝ wavelength EFF probe, grounded via an inductive and capacitive tuning device, was used to converge the RF field at the exposed metal tip of the probe. The probe tip was constructed from a stylet of a 23 gauge stainless steel spinal puncture needle with a diameter of 0.2 mm. Except for the tip, the probe was covered with polyethylene tubing such that the length of the covering could be altered to adjust the length of the exposed metal tip.

A total of 96 Sprague-Dawley rats were used for two types of aneurysm models and an additional 15 Sprague-Dawley rats were used for a third type of aneurysm model. In the first model, abdominal aneurysms were created by side-to-side anastomosis between the abdominal aorta and the inferior vena cava. In the second model, abdominal aneurysms were created by anastomosis between the abdominal aorta of one rat and the donor abdominal aorta from another rat. In the third model, renal vein aneurysms were created by ligation of the renal vein proximal to the van cava. In each case, the rat was anesthetized with 10 mg of ketamine hydrochloride per 100 grams of body weight intramuscularly. Anesthesia was maintained by inhalation of methoxifluoride anesthetic.

Short and long term effects after treatment were observed. All of the aneurysms were treated immediately after the preparation of the aneurysm at the time of the original surgery unless otherwise specified. Observations of acute and chronic effects included visualization of shrinkage and/or collapse of the aneurysm. Aneurysms observed for acute effects were resected immediately after treatment and were submitted for histology. Aneurysms observed for chronic effects were resected three days and three weeks after treatment and were submitted for histology. At the time of histological examination, all aneurysms were observed for complete obliteration of the aneurysm sac and patency of the parent artery. Of the second model, 12 rats served as controls. The average dimensions of the aneurysms were 4 mm×2 mm. Three weeks after the aneurysms were prepared, the abdominal cavities were opened and aneurysm dimensions were measured while being observed under a microscope. Of the first model, 48 rats were observed for acute effects immediately after treatment. The average dimensions of the aneurysms were 7 mm×3 mm. Of the second model, 8 rats were observed for acute effects immediately after treatment. The average dimensions of these aneurysms were 4.8×2.6 mm. Of the first model, 8 rats were observed three days after treatment. The average dimensions of the aneurysms were 5.0 mm×2.7 mm. Of the second model, 11 rats were observed for chronic effects three days after treatment. The average dimensions of these aneurysms were 4.9×2.5 mm. Of the second model, 6 rats were observed for chronic effects 3 three weeks after the treatment. The average dimensions of the aneurysms were 4.7 mm×1.5 mm. Of the second model, 3 control rats were treated three weeks after the preparation of the aneurysms and were observed for chronic effects three weeks after treatment. The average dimensions of these aneurysms were 5.6 mm×2.0 mm.

During surgical treatment, the solenoidal coil was positioned at an average distance of 3 cm from the aneurysm. This distance was found to be optimal for aneurysm thrombosis. The probe was then inserted into the aneurysm and an average power of 98 watts was delivered over a fractionated time at 1 second intervals until the aneurysm was found to be totally thrombosed. Insertion of the probe through the entire length of the aneurysm was found to be necessary for total thrombosis. The length of the exposed tip of the probe is determined by the length of the aneurysm. The exposed tip can be varied by moving the polyethylene sheath longitudinally along the metal needle. During withdrawal of the probe, the sheath is left in place for about 3 to 4 minutes after the probe is removed. This serves to apply counterpressure at the puncture site and prevents bleeding at this site.

Quick and complete thrombosis of the aneurysms was observed during the procedure. The average exposure time totaled about 6 seconds for complete thrombosis. With proper positioning of the needle, preservation of the parenn vessel was obtained without any evidence of kinking or stenosis. It was also observed during the initial study that if the heat was delivered continuously, it tended to cause the blood to expand and explode the aneurysms; hence, a fractionated intense heat was delivered at intervals of 1 second which prevented rupture of the aneurysm. Insertion of the probe along the entire length of the aneurysm was essential for thrombosis.

A total of 56 aneurysms were resected and histologically examined. Twenty-three of the histologically examined aneurysms were observed for chronic effects, and 33 of the aneurysms were observed for acute effects. In addition to histological examination, five days after treatment, angiograms were performed on 9 of the second model rats in which chronic effects were observed three days after treatment, and one of the untreated rats three days after aneurysms were created.

EXAMPLE III

In a manner analogous to the previous Examples, studies were conducted using 38 Sprague Dawley rats weighing an average of 350 grams and four C3H mice weighing an average of 28 grams that had subcutaneously implanted mammary carcinoma. The average diameter of these subcutaneous tumors were 1.7 cm. The animals were anesthetized with ketamine hydrochloride intraperitoneally using a dosage of 7.2 mg. per kilogram of body weight and maintained by inhalation of methoxy flurane. At the end of the study the animals were sacrificed by overdosing them with ketamine hydrochloride. Four different studies were performed on the above animals by dividing them into four different groups.

Group (1)—Study of Coagulation, Cutting and Vaporizing Effect on Brain Tissue In 33 of the above rats, bilateral large craniectomies were performed. The dura was opened and the animals were brought in the electromagnetic field. Cortical incisions were made by running the EFF probe gently over the surface of the brains. One to two cuts were made on each side. Coagulation of the surface vessels in the area of the cortical incision were observed. Some cortical vessels were coagulated by touching the probe to the vessel. In six of these animals, frontal lobectomies were also performed by vaporizing the brain using the probe. The above studies were done using 100 and 130 wattage. The cutting effect and vaporizing effect were also studied under saline. In 3 rats, the abdominal cavities were opened and the large abdominal vessels including the inferior vena cava and the abdominal aorta were coagulated. Twenty-five rats were sacrificed immediately following the studies; five, two days after the studies; one, three days after the studies and two, four days after the studies. The brains of these animals were then fixed in 10% formaldehyde for five days and histological studies were then performed using H & E stain.

Group (2)—Study of Blood Brain Barrier Disruption

Using Evans blue dye, 11 of the above rats in Group (1) Study were used for the study of blood brain barrier disruption. Prior to making the lesions, the abdominal cavity was opened through a midline incision and 0.9 cc of 2% Evans blue dye in normal sline was infected into the inferior vena cava. A 10 minute interval was given for protein binding prior to making the lesions. After lesions were created, an interval of 30 minutes was given and then photographs of the brain surface and brain sections perpendicular to the cortical incisions were taken for colored slides. Spread of this dye into the surrounding tissue was then isualized and mapped onto the histology slides. Also, the thickness of the dye spread was measured.

Group (3)—Study of Heat Dissipation

Five rats were used for this study. After bilateral craniectomies were performed, a Luxtron fluroptic temperature sensing probe (manufactured by Luxtron, Mountain View, Calif.) was inserted to a depth of 3 mm. into the brain. The EFF probe was then inserted at a depth of 3 mm. circumferentially in different sectors of the brain around the temperature sensing probe at distances of 2 mm., 5 mm. and 7 mm. from the temperature sensing probe and 130 watts of power was delivered for each position for 10 seconds. Temperature was recorded for each probe position at an interval of 2 seconds up to 10 seconds duration. Ten seconds mzimum duration was chosen because a maximum temperature rise was noted at 10 seconds for this depth of penetration of EFF probe. The EFF probe was changed to a new position during this study only after the temperature of the temperature sensing probe had returned to the normal temperature of the brain.

Group (4)—Tumor Vaporization Study

The 4 mice with subcutaneous tumors were used for this study. After making an incision on the skin over the tumor and exposing the tumor, vaporization of the tumor was carried out by running the probe gently and quickly over the surface of the tumor. Vaporization was also carried out under saline to study the effectiveness of the probe working under water.

RESULTS

Group (1) A. Coagulating Property

Coagulating property depended upon the wattage used. At a wattage of 100, one could coagulate a vessel up to 2 mm. in diameter. At a wattage of 130, a vessel up to 0.5 mm. could be coagulated. As most of the surface vessels were 0.5 mm. or less in diameter during cortical incision, these vessels were coagulated. This coagulating property was also observed while working under saline.

B. Cutting

Excellent cutting of the brain surface was observed. The histological sections taken perpendicular to the cortical incisions indicated that the breadth of the lesions was slightly larger than the probe diameter. Using a probe diameter of 0.3 mm. a lesion whose breadth was 0.46 mm. was produced. With a wattage of 100, minimal or no edema in the surrounding tissue was observed. At a wattage of 130, however, minimal area of edema measuring 0.19 mm. in breadth on either side of the lesion was observed.

C. Vaporizing Effect

Excellent cerebral vaporization was seen using the system. It was equally effective under saline. The vaporization was best achieved by quick movement of the probe which prevented any char formation on the probe surface. Presence of debris and blood did tend to increase char formation. Higher wattage reduced the amount of char formation.

Group (2)

Very minimal disruption of the blood brain barrier was seen during cortical incision. Dark staining was confined completely to the coagulum within the lesion which measured 0.15 mm. in thickness on each edge of the lesion and very minimal light staining was seen in an area whose thickness measured 0.19 mm. on either side of the lesion.

Group (3)

Results of heat dissipation studies were graphed. At 2 seconds duration, there was practically no dissipation of the heat even at the 2 mm. location from the heating probe. At 5 mm. from the center of the heating, no dissipation was seen even at 10 seconds.

Group (4)

Excellent tumor vaporization was observed with quick movement of the probe. The minimal charring effect seen on the probe tip was further reduced using higher wattage. Generally, debris or stagnant blood tended to increase the charring. Sucking this out of the way reduces the charring to bare minimum. Very minimal or practically no bleeding was observed during vaporization of these tumors. Quick vaporization could be obtained and an average of 10 minutes was required for debulking a mass of 1 cm. diameter using a wattage of 120. Vaporization could be carried out under saline. While working under saline, the exposed tip of the probe should be kept to bare minimum as larger exposure of the tip would result in dissipation of the heat through the saline.

EXAMPLE IV

Ten New Zealand white rabbits were used for vaporization of VX-2 brain tumor with the electromagnetic field focusing probe, as previously described. The rabbits were anesthetized with 100 mg/Kg ketamine hydrochloride intramuscularly. Anethesia was maintained with 15 mg/Kg Nembutal IV.

An 8 mm. skin incision was made over the right side of the cranium. A (0.3 mm) drill was used to make a small burr hole through which an 8 mm long catheter was inserted. A 23 gauge stylet was used to push a small fragment of VX-2 tumor (1 mm.×1 mm.), through the catheter. The catheter was left in place and anchored to the skull by means of a plastic button. The skin was then closed.

Three weeks later, the incision was opened. The plastic button was removed and a craniectomy (1 cm×1 cm) was performed over the area of the catheter. A cortical incision around the area of the catheter was made. The catheter was removed. A suction and the electromagnetic field focusing probe were used to dissect through the brain tissue to the tumor along the track of the catheter. The EFF probe was used for cortical incision, and coagulation of small blood vessels during the dissection.

A small piece of VX-2 tumor was excised and submitted for pathology for tumor verification. The EFF probe was then used to vaporize the tumor. A piece of gel foam was placed over the brain where the craniectomy had been performed and the overlying skin was sewn. The rabbits were allowed to live for three days at which time they were sacrificed with an overdose of Nembutal IV. The brains were immediately resected and submitted to pathology for histological examination of the effects of heat upon surrounding brain tissue, and possible edema.

The probe worked as an excellent tool for cortical incision, coagulation of vessels and vaporization of tumors. The probe was also able to coagulate bleeding vessels by gentle guided contact of the probe. Histological study showed no evidence of hemorrhage or edema in the surrounding brain.

As a result of the Examples, it is concluded that radio frequency electromagnetic field focusing in biological tissue by use of a grounded, tuned probe is a highly effective method of focusing heat and producing highly localized high temperatures. It should also be highly evident in view of the Examples, that such techniques and apparatus are effective as a surgical scalpel, tissue vaporization instrument as well as thrombosis and/or aneurysm shrinking device. It is also established that the surgical treatment according to the present invention is accomplished quickly without effecting the patency of surrounding tissue and without inducing significant bleeding. It is the combination of these features that is felt to represent truly unexpected results relative to the prior art equipment and surgical techniques.

Other specific applications of the apparatus and method according to the present invention are felt to be numerous and beneficial. As such, the present invention is felt to be useful in, by way of example, but not limited thereto: general surgery (including tumor and cyst removal as well as resection of internal organs such as lobectomy, appendectomy, removal of polyps); neurosurgery (including cauterizing lesions and blood vessels, vaporization of tumorous tissue and the like); shrinkage and embolization of aneurysms; vaporizing tumorous growths (including brain and spinal cord); debulking large volume tumors; removal (vaporization) of atherosclerotic plaque in arteries and intracranial tumor or the like; treatment of esophogeal varies; cornea cutting and cataract removal as well as other surgical treatments.

The advantages and benefits associated with the use of the radio frequency surgical tool, or, more generally, the electromagnetic field focusing (EFF) probe according to the present invention are felt to be numerous and significant. Unlike the conventional scalpel, cutting with the EFF probe is inherently accompanied by cauterization so that hemostats are not necessary. Similarly, the use of the conventional $CO_2$ laser to cut living tissue does not inherently solve coagulation. In contrast, the EFF probe cuts and coagulates simultaneously. The advantage of the EFF probe over the YAG laser is that the YAG laser is an excellent coagulator, but does not cut. And, both the $CO_2$ and YAG laser experience problems with beam front control resulting in the possibility of accidental cutting or coagulating of surrounding healthy tissue. Because of the precise focusing of the RF energy associated with the use of the EFF probe, the present invention is superior to the conventional electrocoagulator resulting, for example, in significantly less blood brain barrier (BBB) disruption from the EFF probe treatment of brain lesions. Also, the size of the induced lesion (the incision) relative to the probe diameter and size of the thermocoagulation associated with the use of the EFF probe, according to the present invention, is either comparable or superior to the use of the $CO_2$ laser.

Having thus described the invention with a certain degree of particularity, it is manifest that many changes may be made in the details without departing from the spirit and scope of this disclosure. It is understood that the invention is not limited to the exemplified embodiments set forth herein, but is to be limited only by the scope of the attached claims, including the full range of equivalents to which each element thereof is entitled.

We claim:

1. A method of surgical treatment comprising the steps of:
   (a) creating an electromagnetic field in the vicinity of tissue to be surgically treated; and
   (b) touching the tissue to be surgically treated with the exposed metal tip of a grounded electric current tunable electromagnetic field focusing probe such as to instantaneously vaporize the tissue being contacted by the metal tip and producing simultaneously a cutting and cauterizing effect.

2. A method of surgical treatment comprising the steps of:
   (a) creating an electromagnetic field in the vicinity of tissue to be surgically treated;
   (b) touching the tissue to be surgically treated with the exposed metal tip of a grounded electric current tunable electromagnetic field focusing probe such as to instantaneously vaporize the tissue being contacted by the metal tip and producing simultaneously a cutting and cauterizing effect; and
   (c) removing the vaporized tissue from the region of the surgical treatment by applying a vacuum near the metal tip of said grounded electromagnetic field focusing probe.

3. A surgical tool comprising:
   (a) a radio frequency source means for creating an electromagnetic field in the vicinity of tissue to be surgically treated; and
   (b) an electromagnetic field focusing probe means having a tip focusing the radio frequency energy produced by said radio frequency source means at the region of the tissue making contact with the tip of said electromagnetic field focusing probe means such that the tissue being contacted is instantaneously vaporized, producing simultaneously a cutting and/or cauterizing effect, said probe means being a conductive metal probe covered with an insulating sheath wherein the tip of the conductive metal probe is exposed at one end such as to allow the tip to make contact with the tissue to be surgically treated and wherein the other end of the conductive metal probe is electrically grounded;
   (d) a current monitor means for measuring the electrical current induced in the conductive metal probe; and
   (e) a vacuum tube means adjacent to said conductive metal probe and terminating near the tip of said conductive metal probe such as to remove vaporized tissue during use of said surgical tool.

4. A surgical tool comprising:
   a radio frequency source means for creating an electromagnetic field in the vicinity of tissue to be surgically treated, wherein said radio frequency source means comprises:
   (a) a signal generator means for producing an oscillating electrical signal of a pre-selected frequency;

(b) an amplifier means connected to said signal generating means for amplifying the oscillating electrical signal;
(c) a meter means for monitoring the amplified oscillating electrical signal output;
(d) an inductive applicator means;
(e) an impedance matching means for adjusting the impedance of said amplified oscillating electrical signal output to said inductive applicator means, for inducing the electromagnetic field in the vicinity of the tissue to be surgically treated;
(f) an electromagnetic field focusing probe means, having a tip for focusing the radio frequency energy produced by said radio frequency source means at the region of the tissue making contact with the tip of said electromagnetic field focusing probe means such that the tissue being contacted is instantaneously vaporized, producing simultaneously a cutting and/or cauterizing effect, said probe means being a conductive metal probe covered with an insulating sheath wherein the tip of the conductive metal probe is exposed at one end such that as to allow the tip to make contact with the tissue to be surgically treated and wherein the other end of the conductive metal probe is electrically grounded and including in series between the said tip and said ground:
(1) a current monitor means for measuring the electrical current induced in the conductive metal probe during use of said surgical tool, and
(2) a tuner circuit means for adjusting and optimizing the inducted electrical current passing through said conductive metal probe; and said tool further including
(g) a vacuum tube means adjacent to said conductive metal probe and terminating near the tip of said conductive metal probe such as to remove vaporized tissue during use of said surgical tool.

5. A surgical tool comprising the combination of:
(a) a radio frequency source means for creating an electromagnetic energy field in the vicinity of tissue to be surgically treated; and
(b) a separate electromagnetic field focusing insulated conductive metal probe means having an uninsulated and exposed tip as a focusing means at the region of the tissue making contact with the tip of said probe means, the diameter and length of said exposed tip such that the tissue being contacted is instantaneously vaporized, producing simultaneously, a substantially bloodless cutting and/or cauterizing effect; means for adjusting the optimizing the energy passing through said probe means; and said probe means further including a current monitor means for measuring the electrical current induced in the conductive metal probe means during use of said surgical tool.

6. A surgical tool of claim 5 including a vacuum means adjacent to said conductive metal probe means and terminating near said tip of said conductive metal probe means to remove vaporized tissue during use of said surgical tool.

7. A surgical tool comprising the combination of:
(a) a radio frequency source means for creating an electromagnetic energy field in the vicinity of tissue to be surgically treated; and
(b) a separate electromagnetic field focusing insulated conductive metal probe means having an uninsulated and exposed tip as a focusing means at the region of the tissue making contact with the tip of said probe means, the diameter and length of said exposed tip such that the tissue being contacted is instantaneously vaporized, producing simultaneously, a substantially bloodless cutting and/or cauterizing effect, said probe means being grounded and including in series between said tip and said ground;
(1) a tuner circuit means for adjusting and optimizing the energy passing through said probe means; and
(2) a current monitor means for measuring the electrical current induced in the conductive means probe means during use of said surgical tool.

8. The surgical tool of claim 7 wherein said exposed tip of said conductive metal probe means is a stainless steel needle.

9. The surgical tool of claim 7 including a vacuum tube means adjacent to said probe means and terminating near said tip of said probe means to remove vaporized tissue during use of said surgical tool.

10. A surgical tool of claim 7 wherein said conductive metal probe means is of size to be insertable intravenously.

11. A surgical tool of claim 7 wherein said radio frequency source means further comprises:
(a) a signal generator means for producing an oscillating electrical signal of a pre-selected frequency;
(b) an amplifier means connected to said signal generating means for amplifying the oscillating electrical signal;
(c) a meter means for monitoring the amplified oscillating electrical signal output;
(d) an inductive applicator means for inducing the electromagnetic field in the vicinity of the tissue to be surgically treated; and
(e) an impedance matching means for adjusting the impedance between said amplifier means and said inductive applicator means.

12. The surgical tool of claim 11 including
(f) means to adjust said frequency to effect said surgical treatment.

13. The surgical tool of claim 12 wherein said frequency is within the range of 13.0 to 28.0 MHz.

14. The surgical tool of claim 11 wherein said exposed tip of said conductive metal probe means is a stainless steel needle.

15. The surgical tool of claim 11 including a vacuum tube means adjacent to said probe means and terminating near said tip of said probe means to remove vaporized tissue during use of said surgical tool.

16. A surgical tool of claim 11 wherein said conductive metal probe means is of size to be insertable intravenously.

17. A tool for surgical use in vaporizing artheroschlerotic plaque in animal and human patients comprising:
an electromagnetic field focusing insulated conductive metal probe means capable of insertion intravenously, said probe means having an exposed heatable tip means for receiving radio frequency (RF) waves, while said heatable tip means is intravenously positioned adjacent said plaque, to raise the temperature of said heatable tip means sufficient to vaporize said plaque;
a ground wire electrically connected to said heatable tip means and adapted to be connected to an electrical ground external of said patient into which said probe means is inserted; and means separate and removed from the probe means for transmitting RF waves toward said patient, said heatable tip means when grounded by said ground wire acting to focus said RF waves to instantaneously raise the temperature of said heatable tip means.

18. The surgical tool of claim 17 wherein said exposed heatable tip means of said probe means is a stainless steel needle.

19. The surgical tool of claim 17 including a vacuum tube means adjacent said conductive metal probe means which terminates near said heatable tip means so as to remove vaporized plaque during use of said tool.

20. A surgical tool of claim 7 wherein said probe means is of size to be insertable intravenously.

21. The tool of claim 17 wherein said means for transmitting said RF waves includes:
  (a) a signal generator means for producing an oscillating electrical signal of a pre-selected frequency;
  (b) an amplifier means connected to said signal generating means for amplifying the oscillating electrical signal;
  (c) a meter means for monitoring the amplified oscillating electrical signal output;
  (d) an inductive applicator means, for inducing the electromagnetic field in the vicinity of the tissue to be surgically treated;
  (e) impedance matching means for adjusting the impedance between said inductive applicator means and said amplified oscillating electrical signal output; and
  (f) means to select said frequency; and wherein said metal probe means includes in series between each end:
    (1) a current monitor means for measuring the electrical current induced in the conductive metal probe means during use of said tool, and
    (2) a tuner circuit means to adjust and optimize the induced electrical current passing through said conductive metal probe means.

22. The surgical tool of claim 21 wherein said exposed heatable tip means of said conductive metal probe means is a stainless steel needle.

23. The surgical tool of claim 21 including a vacuum tube means adjacent said conductive metal probe means which terminates near said heatable tip means so as to remove vaporized plaque during use of said tool.

24. A surgical tool of claim 21 wherein said conductive metal probe means is of size to be insertable intravenously.

* * * * *